US010791908B2

(12) United States Patent
Au

(10) Patent No.: US 10,791,908 B2
(45) Date of Patent: Oct. 6, 2020

(54) SYSTEMS AND METHODS FOR MEDICAL INSTRUMENT FORCE SENSING

(71) Applicant: Intuitive Surgical Operations, Inc., Sunnyvale, CA (US)

(72) Inventor: Samuel Kwok Wai Au, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 843 days.

(21) Appl. No.: 15/505,856

(22) PCT Filed: Aug. 21, 2015

(86) PCT No.: PCT/US2015/046353
§ 371 (c)(1),
(2) Date: Feb. 22, 2017

(87) PCT Pub. No.: WO2016/032902
PCT Pub. Date: Mar. 3, 2016

(65) Prior Publication Data
US 2017/0273542 A1 Sep. 28, 2017

Related U.S. Application Data

(60) Provisional application No. 62/041,204, filed on Aug. 25, 2014.

(51) Int. Cl.
*A61B 5/05* (2006.01)
*A61B 1/00* (2006.01)
(Continued)

(52) U.S. Cl.
CPC ........ *A61B 1/00006* (2013.01); *A61B 1/0016* (2013.01); *A61B 1/0051* (2013.01);
(Continued)

(58) Field of Classification Search
None
See application file for complete search history.

(56) References Cited

U.S. PATENT DOCUMENTS 6,380,732 B1   4/2002  Gilboa
6,389,187 B1   5/2002  Greenaway et al.
(Continued)

FOREIGN PATENT DOCUMENTS

CN        101642364 A      2/2010

OTHER PUBLICATIONS

Extended European Search Report for Application No. EP15836047.9, dated Apr. 5, 2018, 9 pages.
(Continued)

*Primary Examiner* — Joel F Brutus
(74) *Attorney, Agent, or Firm* — Haynes & Boone, LLP

(57) ABSTRACT

A method, and associated system, includes receiving inputs from a medical instrument having at least one elongated actuation element used to manipulate a position of the instrument. The method also includes determining a force on a tip of the medical instruments by applying the inputs to a lumped model of the instrument, the lumped model comprising a mass of a motor user to operate the at least one elongated actuation member and a mass of at least a portion of a catheter body of the medical instrument.

18 Claims, 5 Drawing Sheets

(51) Int. Cl.
    *A61B 5/06*     (2006.01)
    *A61B 1/005*     (2006.01)
    *A61B 34/37*     (2016.01)
    *A61B 34/30*     (2016.01)
    *A61B 34/00*     (2016.01)
    *A61M 25/00*     (2006.01)
    *A61M 25/01*     (2006.01)
    *A61B 34/20*     (2016.01)

(52) U.S. Cl.
    CPC .......... *A61B 1/00133* (2013.01); *A61B 5/062* (2013.01); *A61B 5/065* (2013.01); *A61B 34/30* (2016.02); *A61B 34/37* (2016.02); *A61B 34/71* (2016.02); *A61M 25/0067* (2013.01); *A61B 2034/2061* (2016.02); *A61B 2034/301* (2016.02); *A61B 2034/742* (2016.02); *A61B 2562/0247* (2013.01); *A61B 2562/0266* (2013.01); *A61M 2025/0166* (2013.01)

(56) References Cited

U.S. PATENT DOCUMENTS

| | | | |
|---|---|---|---|
| 7,316,681 | B2 | 1/2008 | Madhani et al. |
| 7,720,322 | B2 | 5/2010 | Prisco |
| 7,772,541 | B2 | 8/2010 | Froggatt et al. |
| 7,930,065 | B2 | 4/2011 | Larkin et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 2005/0154262 | A1* | 7/2005 | Banik ................ A61B 1/00059 600/179 |
| 2006/0013523 | A1 | 1/2006 | Childlers et al. |
| 2010/0030023 | A1 | 2/2010 | Yoshie |
| 2010/0168620 | A1 | 7/2010 | Klimovitch et al. |
| 2011/0319714 | A1 | 12/2011 | Roelle et al. |
| 2012/0123441 | A1 | 5/2012 | Au et al. |
| 2012/0316407 | A1 | 12/2012 | Anthony et al. |
| 2013/0172784 | A1 | 7/2013 | Kirschenman |
| 2014/0275997 | A1* | 9/2014 | Chopra ................ A61B 5/064 600/424 |

OTHER PUBLICATIONS

International Preliminary Report on Patentability for Application No. PCT/US2015/046353, dated Mar. 9, 2017, 7 pages.
International Search Report and Written Opinion for Application No. PCT/US2015/046353, dated Nov. 23, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEMS AND METHODS FOR MEDICAL INSTRUMENT FORCE SENSING

RELATED APPLICATIONS

This patent application claims priority to PCT Application No. PCT/US15/46353 filed Aug. 21, 2015 which claims priority to and the benefit of the filing date of U.S. Provisional Patent Application 62/041,204, entitled "SYSTEMS AND METHODS FOR MEDICAL INSTRUMENT FORCE SENSING," filed Aug. 25, 2014, which is incorporated by reference herein in its entirety.

FIELD

The present disclosure is directed to systems and methods for tracking a medical device within a patient anatomy during a medical procedure, and more particularly to systems and methods for efficiently determining pressure on the tip of a medical instrument while the instrument is inside the patient.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive medical procedures may rely upon instrument position monitoring to ensure proper access to, and behavior at, the target tissue location. For some procedures, a minimally invasive medical instrument may navigate natural or surgically created passageways in anatomical systems to reach the target tissue location. For example, a minimally invasive medical instrument may navigate natural passageways in the lungs, the colon, the intestines, the kidneys, the heart, the circulatory system, or the like. Some minimally invasive medical instruments may be teleoperated or otherwise computer-assisted.

Accurate medical instrument models are useful in the design, stability analysis, and real-time operation of the instrument control systems. Often, instrument modeling relies upon continuous numerical modeling techniques such as finite element analysis (FEA). These techniques are often computationally expensive and require significant variable parameter fitting and tuning. Because of the computational complexity associated with these systems, it is often not feasible to use them for real time modeling or predicting tissue interaction forces at the instrument tip for control and monitoring applications. Improved systems and methods are needed for predicting the interaction forces between the instrument tip and surrounding tissues for control, monitoring, and safety applications.

SUMMARY

The embodiments of the invention are summarized by the claims that follow below.

In one embodiment, a method for determining force on a tip of an instrument includes receiving inputs from a medical instrument having at least one elongated actuation member used to manipulate a position of the instrument while in a patient's body, applying the inputs to a lumped model of the instrument, and determining a force on a tip of the instrument based on both the inputs and the lumped model.

In another embodiment, a processing system includes a processor and a memory having computer readable instructions stored thereon, the computer readable instructions, when executed by the processor, cause the system to receive inputs from a motor attached to an elongated actuation member within a medical instrument, the elongated actuation member used to manipulate a position of a tip of the medical instrument. The system is further to receive an input indicating a position of the tip of the medical instrument, apply the inputs to a model of the medical instrument, and use the inputs with the model to determine a force placed on a tip of the instrument from a patient's tissue.

In another embodiment, a medical system includes a medical instrument that includes a catheter body having a tip at a distal end, at least one motor having a rotating member, and a cable wrapped around the rotating member and extending from the rotating member through the medical instrument and configured to manipulate a position of the catheter body tip. The system further includes a control system configured to receive an input indicating a position of the motor, receive an input indicating a force on the motor, receive an input indicating a position of the catheter body tip, and determine, in real time, a force on the catheter body tip based on the inputs and a model of components of the instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
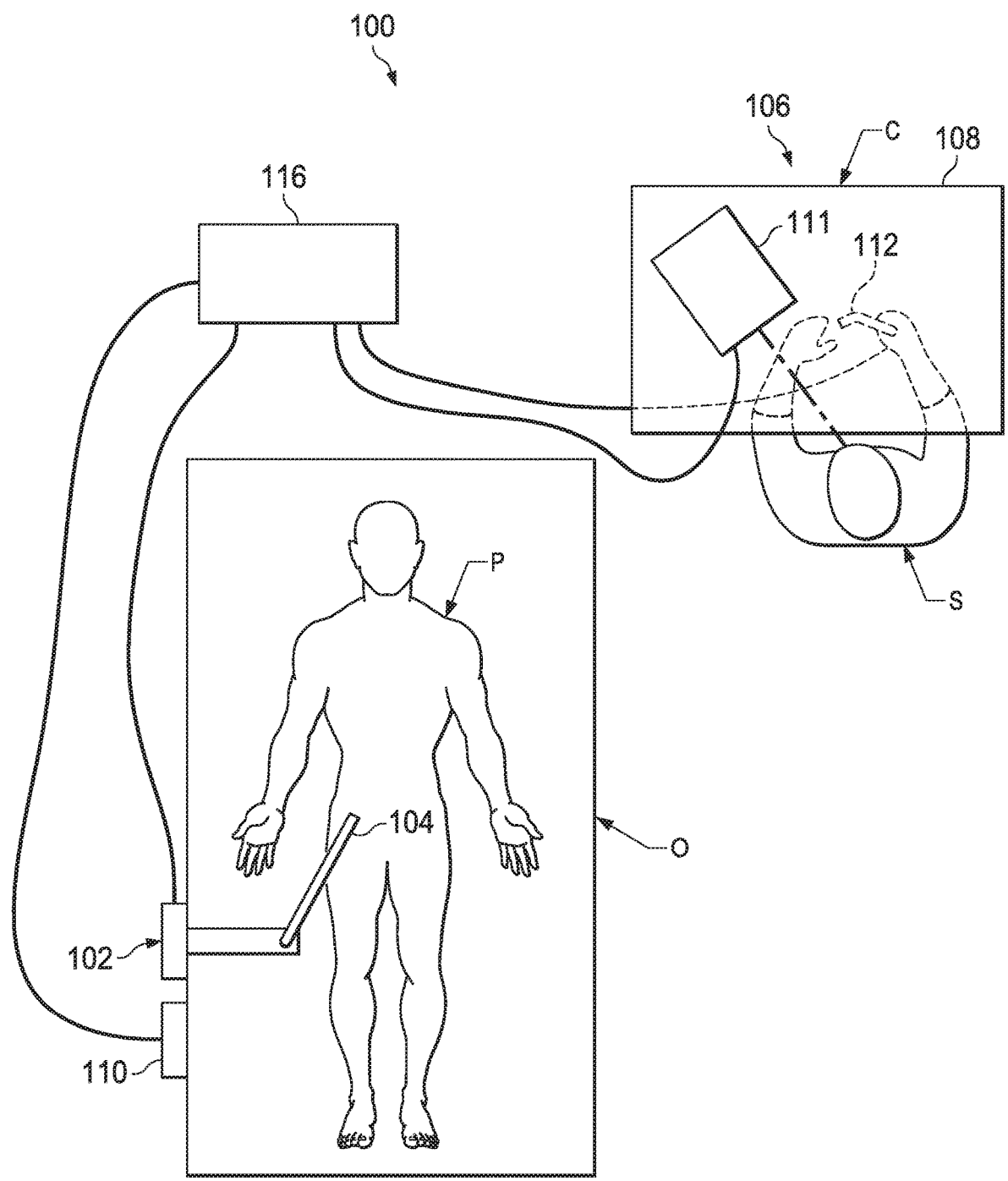
FIG. 1 is a teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console C, which is usually located in the same room as operating table O. However, it should be understood that the surgeon S can be located in a different room or a completely different building from the patient P. Operator input system 106 generally includes one or more control device(s) 112 for controlling the medical instrument system 104. The control device(s) 112 may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) 112 will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) 112 may have more or fewer degrees of freedom than the associated medical instruments and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 116). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system 110 for capturing images from the distal end of the catheter system.

The visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 100 includes endoscopic components that may be integrally or removably coupled to the medical instrument 104. However in alternative embodiments, a separate endoscope, attached to a separate manipulator assembly may be used with the medical instrument to image the surgical site. The visualization system 110 may be implemented as hardware, firmware, software or a combination thereof which interact with or are otherwise executed by one or more computer processors, which may include the processors of a control system 116 (described below).

The teleoperational medical system 100 also includes a display system 111 for displaying an image or representation of the surgical site and medical instrument system(s) 104 generated by sub-systems of the sensor system 108. The display 111 and the operator input system 106 may be oriented so the operator can control the medical instrument system 104 and the operator input system 106 with the perception of telepresence.

The display system 111 may also display an image of the surgical site and medical instruments captured by the visualization system 110. The display 111 and the control devices 112 may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 111 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 111 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 111 may display a virtual navigational image in which the actual location of the medical instrument is registered with preoperative or concurrent images to present the surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
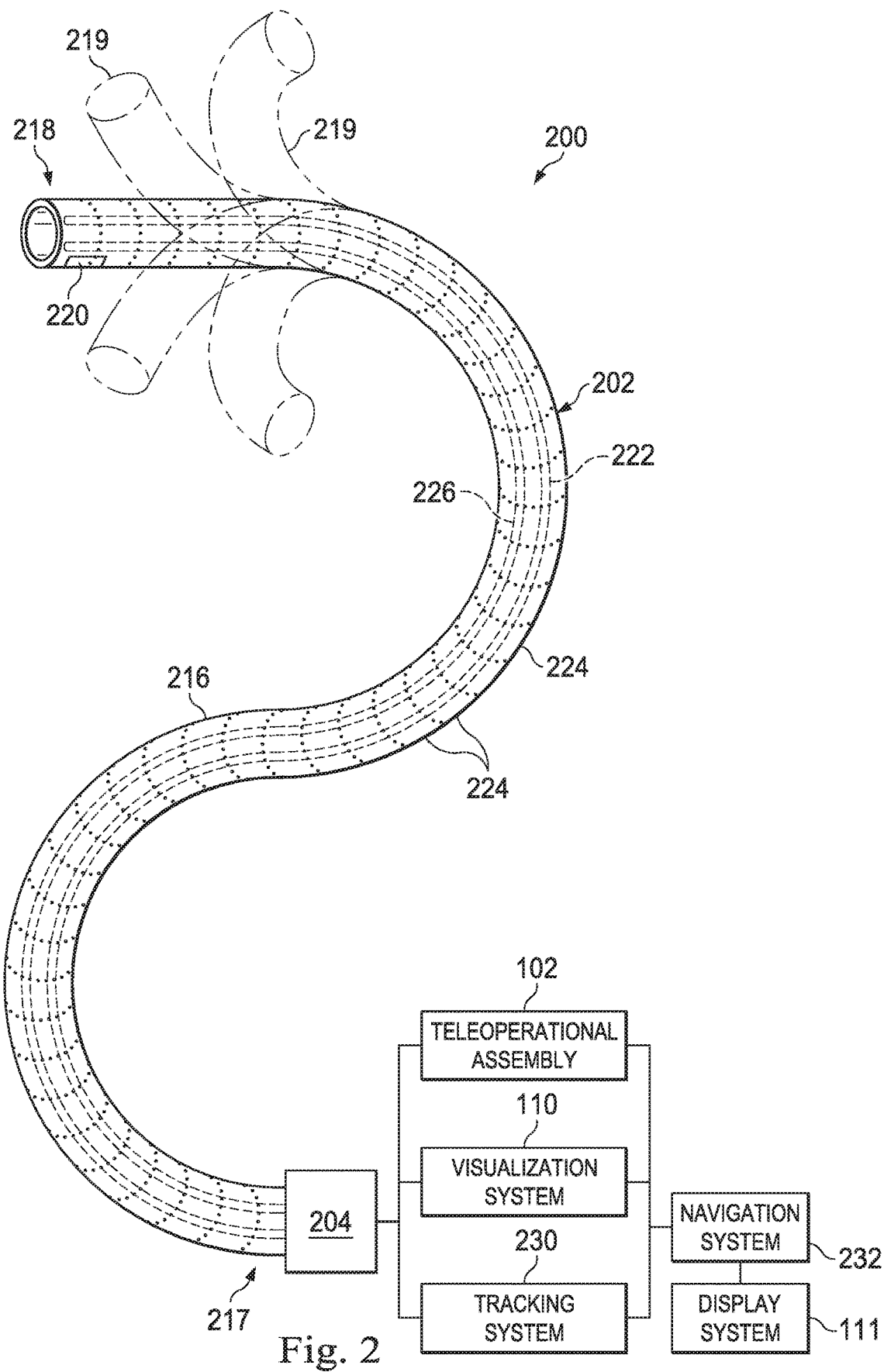
FIG. 2 illustrates a medical instrument system, according to one example of principles described herein.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary, or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths and therefore reflect only this narrow band of wavelengths while passing through a much broader band. During fabrication of the FBGs, the modulations are spaced by a known distance, thereby causing reflection of a known band of wavelengths. When a strain is induced on the fiber core, however, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065 (filed Jul. 20, 2006) (disclosing "Robotic Surgery System Including Position Sensors Using Fiber Bragg Gratings"), which is incorporated by reference herein in its entirety. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by the visualization system 110 for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 110 and/or the preoperatively taken images to provide the surgeon or other operator with real-time position information on the display system 111 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

Dynamic models of an instrument system (e.g., system 200) are useful in guiding controller design and in performing stability analysis. The specifications derived from the controller design may also be used to guide catheter construction and design, thus avoiding a lengthy trial and error process for catheter design and performance verification. Such models may also be used to predict critical system parameters that effect safety. For example, the models may be used to model applied force/torque from tissue in real time, thus preventing or reducing damage to the tissue or to the instrument. Dynamic modeling may be particularly useful with small diameter instruments where large pressure sensors for directly measuring distal tip force are not practical given the space constraints.

Figure 3:
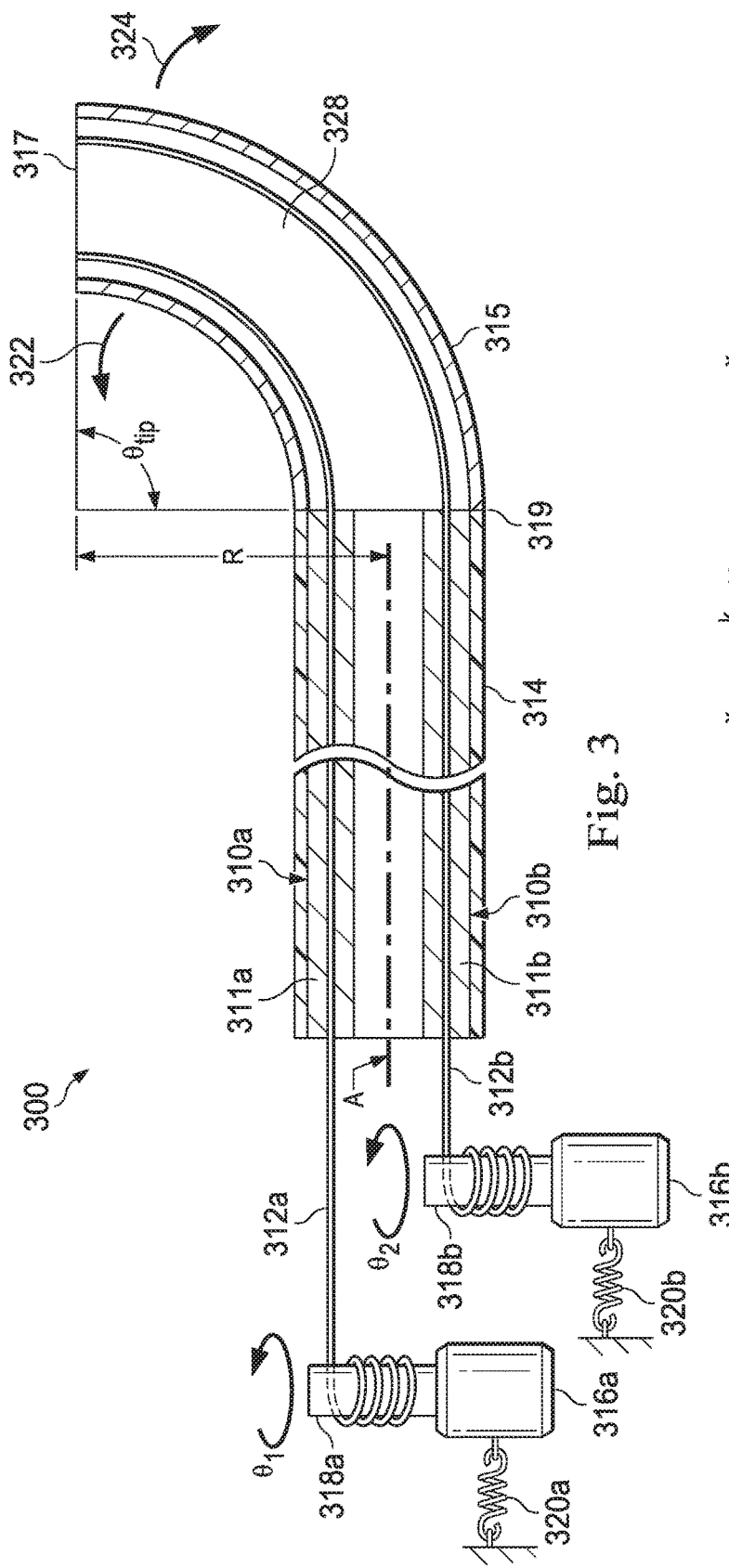
FIG. 3 is a diagram showing an illustrative medical instrument with pull wires, according to one example of principles described herein.

FIG. 3 schematically illustrates a medical instrument system 300, similar to the instrument system 200, with opposing actuation members 310a, 310b extending longitudinally within a flexible catheter body 314 of the instrument 300. The actuation members 310a, 310b move a distal end portion 315 of the flexible body 314 in opposite directions in one degree of freedom (e.g., pitch degree of freedom motion). The flexible body 314 may also house opposing drive components (not shown) for moving a distal tip 317 of the flexible body in opposite directions in other degrees of freedom (e.g. yaw degree of freedom). In this embodiment, the actuation members are tendons, such as pull wires. At least a portion of the tendons 310a, 310b may be formed of Bowden cable having elongated inner components 312a, 312b, respectively, (e.g., a wire or cable) movable with respect to and elongated outer coiled sheaths 311a, 311b, respectively. The tendons 310a, 310b are also designed to have a minimal amount of friction with the interior of the body 314, or any lumens through which the tendons extend. This allows the tendons 310a, 310b to slide as needed during operation and movement of the instrument tip 315. In some examples, the tendons 310a, 310b may be disposed within an inner lumen of the main lumen that forms the body 314.

Each cable 312a, 312b is coupled to a respective drive mechanism 316a, 316b. In this embodiment, the drive mechanisms 316a, 316b are servo motors with drive shafts 318a, 318b, respectively. The cable 312a is wrapped around the drive shaft 318a, and the cable 312b is wrapped around the drive shaft 318b. Distal ends of the actuation members 310a, 310b are connected at or near an instrument distal tip 317. Drive mechanisms 316a, 316b are compliantly coupled through tensioning systems 320a, 320b to a motor housing or to each other. For example, drive mechanism 316a can be tensioned with a spring attached to drive mechanism 316b. The tensioning systems 320a, 320b include a biasing member (e.g. a spring) that apply torsional preload tension to drive components 316a, 316b. The tensioning systems are able to compensate for slack that may develop in the actuation members 310a, 310b.

Rotation of the motors 316a, 316b will either extend or shorten the actuation member distance between the shafts 318a, 318b and the instrument tip 317. The motor shafts 318a, 318b can be rotated in a reciprocal manner such that the distal end portion 315 pivots in a pitch motion about a joint region 319. For example, to move the distal end portion 315 in a pitch direction 322, the motor 316a may rotate the shaft 318a to shorten the distance of the actuation member 310a between the shaft 318a and the instrument tip 317. Additionally, or alternatively, the motor 316b may rotate the shaft 318b so that the distance of the actuation member 310b between the shaft 318b and the instrument tip 315 is extended. Similarly, to move the distal end portion 315 in an opposite pitch direction 324, the motor 316a may rotate the shaft 318a to extend the distance of the actuation member 310a between the shaft 318a and the instrument tip 317. Additionally or alternatively, the motor 316b may rotate the shaft 318b so that the distance of the actuation member 310b between the shaft 318b and the instrument tip 317 is shortened. The distal end portion 315 of the instrument can be moved in pitch as described or in other degrees of movement, such as yaw and roll, to navigate an internal passage of a patient. The amount of angulation θtip between the joint 319 and the distal tip 317 and the offset distance R between the distal tip 317 and a longitudinal axis A defined through the instrument proximal of the joint 319 varies with the pitch of the distal portion 315 and thus with the amount of angular rotation θ1 and θ2 of the motors 316a, 316b, respectively.

The instrument 300 includes a passageway 328 sized for passage of any of a variety of tools to perform various medical procedures. In one example, a biopsy tool may extend through the passageway to remove tissue from the patient through the distal tip 317. The location of specific tissue to be biopsied may have been identified from a pre- or intra-operative CT image. In another example, the instrument 300 may include an imaging device or allow for passage of an imaging device through the passageway 328 to allow a surgeon to visually inspect a target location within an interior passageway of the patient. Thus, instrument tip 317 may navigate internal passageways of a patient to reach a target location.

Figure 4:
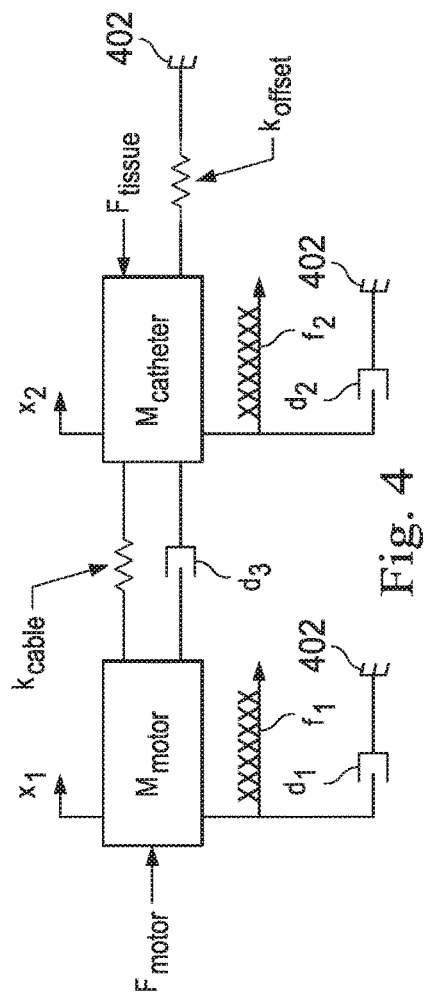
FIG. 4 is a diagram showing an illustrative model of an instrument system, according to one example of principles described herein.

As shown in FIG. 4, the instrument system 300 may be modeled as with a lumped parameter model 400. A lumped model is a simplified description of the behavior of spatially distributed physical systems. It typically uses a topology consisting of discrete entities that approximate the behavior of a distributed system under certain assumptions. A lumped model for a mechanical system typically includes a set of rigid bodies with spring and damping forces between those bodies. As compared to more computationally complex continuous numerical modeling techniques such as FEA, the lumped parameter model 400 is a simple dynamic catheter model that permits real-time modeling of the instrument 300. Thus, the model can be used to provide guidance and feedback to an operator during a medical procedure.

In the model 400, motors 316a, 316b are modeled as a rigid body mass Mmotor subject to a coulomb friction f1 and a viscous friction d1 coupled to ground 402. Ground 402 represents a theoretical fixed, stable body. The frictions f1 and d1 correspond to the frictional forces experienced by the rotating motor shafts. Because the model 400 is a lumped model, f1 and d1 may represent the combined effect of friction experienced by the motor shafts and friction experienced by parts of the cables connected to the motor shafts.

The angular rotation and/or orientations (or change in orientations) of motor shafts 318a, 318b may be modeled as orientation displacement X1. The rotation and/or orientation of the motor shafts can be determined in real time. This may be done, for example, through use of resolvers, encoders, potentiometers, and other mechanisms that can determine rotation and orientation of the motor shafts. The force applied to actuate the motors is modeled as a force Fmotor applied to the mass Mmotor. The pick-up springs 320a/320b, if providing a constant spring force, can be factored into the model by adding a constant to F_motor. If the pick-up springs 320a/320b are linear springs, they can be accounted for using motor position. In some cases, however, the force from the pickup-springs 320a/320b may be so negligible that the model 400 is accurate enough without accounting for the pick-up springs 320a/320b.

The model 400 represents the two motors 316a, 316b as a single rigid body mass, but in alternative embodiments, the motors may be modeled as separate rigid body masses. The two motors 316a, 316b can be simplified by only considering the component of the motion consisting of one motor pulling its pull-wire and the opposite motor releasing its pull-wire. Thus, the two motors 316a/316b can be represented by one mass. The force Fmotor 404 can be monitored in real time. This may be done by calculating the force from the current that is being applied to the motor. In some examples, the current being applied is software controlled. Thus, the current and thus the force can easily be monitored. In some cases, however, a force sensor on the cable or the motor shaft may be used to monitor the motor force Fmotor 404.

All or a portion of the catheter body 314 (and any tools extending therein) is modeled as a rigid body mass Mcatheter subject to a coulomb friction f2 and a viscous friction d2 coupled to ground 402. For example, the mass Mcatheter may represent the tip 317 or the distal end 315. The frictions f2 and d2 correspond to the frictional forces experienced by the catheter body 314 sliding along the anatomical passageways. Frictions f2 and d2 represent the friction of the cable, or part of the cable that slides within the catheter body, as well as the friction in the distal section 315 as the distal section 315 bends. The position and orientation of the distal tip 317 of the catheter (e.g., the angulation θtip and the offset distance R) is modeled as displacement X2. X2 represents θtip and R can be derived from θtip The bending stiffness and the axial stiffness of the catheter body 314 is modeled as a spring with a spring constant koffset coupled between the mass Mcatheter and the ground 402.

The actuation members 310a, 310b are modeled as a spring coupled between the masses Mcatheter and Mmotor. The spring has a spring constant kcable, and a corresponding damper parameter providing viscous friction d3. The model 400 represents the actuation members 310a, 310b as a single element with a single spring and a single damper, but in alternative embodiments, the actuation elements may be modeled as separate rigid body masses.

Figure 5:
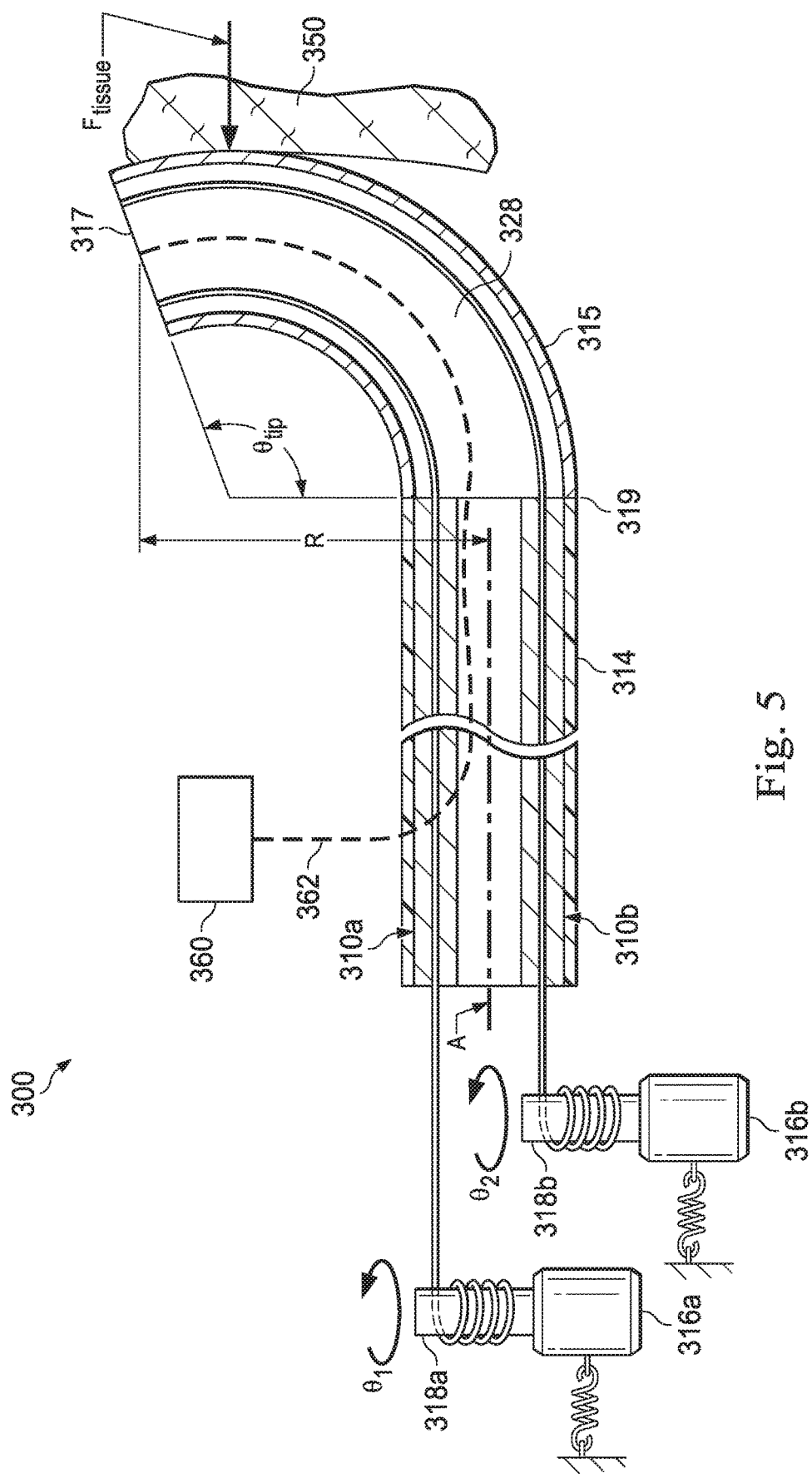
FIG. 5 is a diagram showing an illustrative medical instrument with a position sensor, according to one example of principles described herein.

Referring now to FIG. 5, as the distal end 315 of the instrument 300 moves through the interior passageways of a patient, it encounters human tissue 350. Thus, a force will be applied on the tissue 350 by the distal tip 317 and an equal and opposite force Ftissue will be applied on the distal tip 317 by the tissue 350. As described above, if this force exceeds a predefined threshold, the distal end 315 may cause damage to the tissue 350. For example, the instrument tip 317 may scratch the inner surface of the tissue 350 or may tear a hole in the tissue. Using the model 400, an operator of the medical instrument 300 may know how much pressure or force is being applied to the tissue 350, in real-time. The model 400 thus serves as a dynamic state observer for continuously monitoring the interaction force between the tissue and the instrument.

Referring again to FIG. 4, the force Ftissue of the distal tip 317 on the patient tissue may be determined using the model 400. The parameters force Fmotor, displacement X1, and displacement X2 may be measured throughout the medical procedure and applied to the model to determine the real-time force Ftissue. The force Fmotor applied to the lumped model 400 provides a real-time estimation of the force Ftissue. The frictional parameters f1, f2, d1, d2, d3 and spring parameters kcable and koffset are used to determine other forces at work in the instrument system 300 which influence the force Fmotor to determine the resultant force Ftissue. In some embodiments, the frictional parameters f1, f2, d1, d2, d3 and spring parameters kcable and koffset may be constant for a particular medical instrument used to perform medical procedure on a particular patient. Alternatively, one or more of these parameters may be varied based upon the particular patient at the start of or during a medical procedure. For example, the frictional parameters f2, d2 associated with the friction of the catheter body 314 moving against the passageway may vary with patient age, tissue type, and/or location along the patient anatomical passageway (i.e., passageway may be more rigid in some locations compared to others). Additionally, the shape of the catheter body 314 may be measured, and the shape information used to adjust the values of the spring constant koffset. For example, based on how the catheter body 314 is bent, there may be more or less axial and bending stiffness. Because the model is a lumped model 400, the inertia (mass), stiffness and friction of the catheter and the pull wires depend on the shape of the catheter. For example, the stiffness of the catheter when making a 90 degree bend may be different than the stiffness of the catheter when straight. One way to correct for this effect is to determine the inertia, stiffness and friction parameters (i.e. M_catheter, k_offset, f2, d2, k_cable, d3) with the catheter in a number of different shapes offline, and then use the shape sensor during the procedure to determine which of the offline shapes is most appropriate.

Additionally or alternatively, friction force f2, d2, and d3 can be measured directly by attaching a force sensor at the base of the outer coiled sheaths 311a, 311b. As the proximal part of the catheter (between 318 and 319) changes shape, the correct motor positions for a desired θtip changes. By using the shape sensor, we can measure the catheter shape and determine what the correct motor position should be.

The motion of the system in FIG. 4 follows the relationships: M_motor a1=−d1 v1−f1 sine(v1)+k_cable (x2−x1)+d3 (v2−v1)+F_motor+F_return_spring; and M_catheter a2=−k_offset x2−d2 v2−f2 sine(v2)+k_cable(x1−x2)+d3 (v1−v2)−F_tissue; where v1 (velocity) is the time derivative of x1 and a1 (acceleration) is the time derivative of v1 (similarly for v2, a2, and x2). because we know x1 (motor position), x2 (catheter tip position), and F_motor (force applied by motor), and we can derive v1, v2, a1, and a2 from x1 and x2, and we know d1, d2, d3, M_motor, M_catheter, f1, f12, k_cable, and k_offset from offline experiments, we can deduce F_tissue from the above equations.

FIG. 5 illustrates that in one embodiment, the displacement X2 of the distal tip 317 and/or the shape of the distal end portion 315 may be determined by a position and/or shape sensor. According to the illustrated embodiment, a shape sensor 362 (e.g. shape sensor 222 described above) includes a fiber optic cable extending through the instrument 300. The shape sensor 362 is coupled at a proximal end to an interrogator 360 and extends to the distal tip 317. In alternative embodiments, the sensor may terminate elsewhere in the distal end portion 315. The interrogated shape sensor 362 provides information about the shape of the distal end portion 315, and the shape information may be used to determine the position and orientation of the distal tip 317 relative to another point along the sensor such as the joint 319 or the interrogator 360 which may be fixed relative to the patient anatomy. Additional information regarding the use of optical shape sensors to determine the position of portions of medical instrument is provided in U.S. Pat. No. 7,720,322 (filed Jun. 30, 2008) (disclosing "Fiber Optic Shape Sensor") which is incorporated by reference herein in its entirety.

Figure 6:
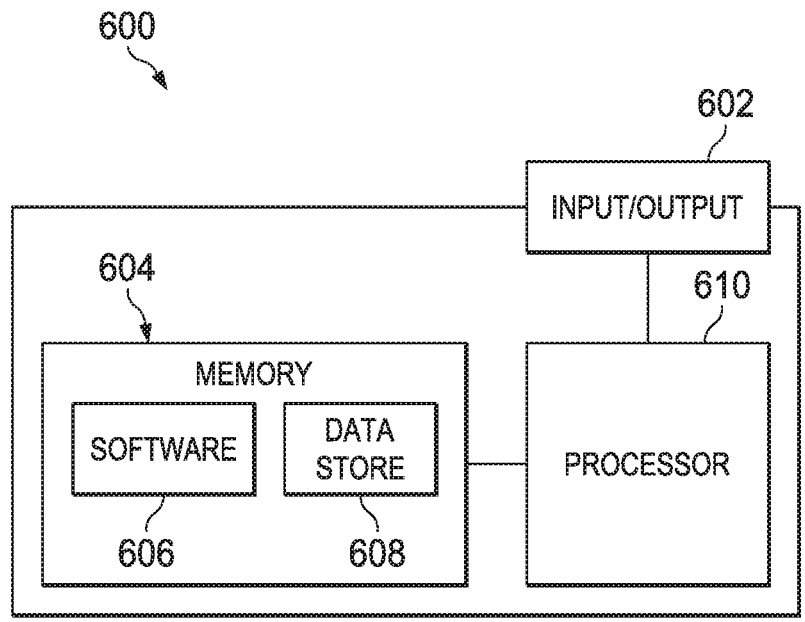
FIG. 6 is a diagram showing an illustrative processing system that can be used with a medical instrument system, according to one example of principles described herein.

FIG. 6 is a diagram showing an illustrative processing system (e.g., control system 116) that can be used with the medical instrument system 300. The processing system 600 includes a memory 604 which may include software 606 and a data store 608. The processing system also includes a processor 610 and an Input/Output (I/O) port 602.

The memory 604 may be one of several different types of memory. Some types of memory, such as solid state drives, are designed for storage. These types of memory typically have large storage volume but relatively slow performance. Other types of memory, such as those used for Random Access Memory (RAM), are optimized for speed and are often referred to as "working memory." The various types of memory may store information in the form of software 606 and data in the data store 608.

The processing system 600 also includes a processor 610 for executing the software 606 and using or updating the data 608 stored in memory 604. The software 606 may include the tools that are necessary to calculate, in real time, an instrument tip force based on a model and a set of inputs. The software may also include a mechanism for alerting an operator of the instrument if the instrument tip force exceeds a predefined value. For example, an operator of the instrument may set a value at which he or she should be alerted if the instrument tip force exceeds that value. This value may be a standard value set by medical industry standards. In some cases, the value may be adjusted based on the nature of the patient. For example, if the operator believes that a patient may be more susceptible to tears in the internal tissue, then the operator may set the value lower so that he or she can be alerted when the instrument tip force exceeds a level that is deemed unsafe for a particular patient.

Figure 7:
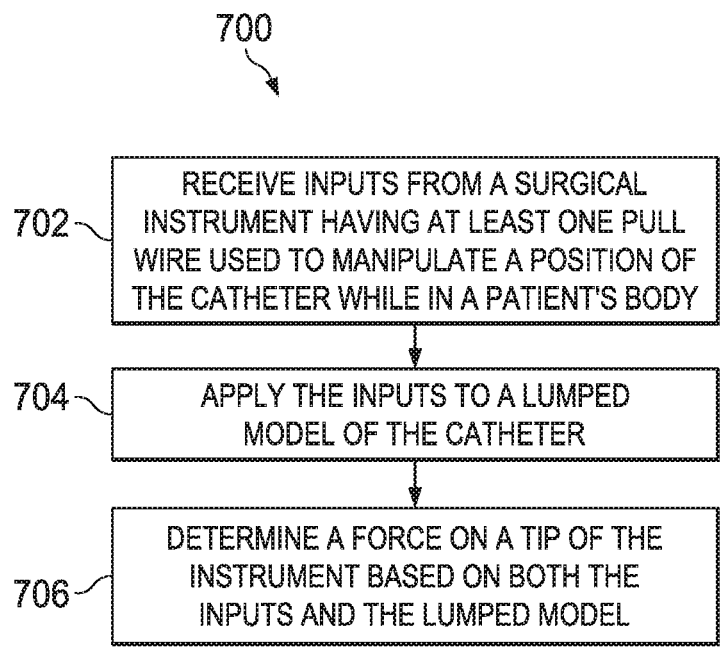
FIG. 7 is a flowchart showing an illustrative method for using a model to monitor tip pressure of a medical instrument, according to one example of principles described herein.

FIG. 7 is a flowchart showing an illustrative method for using a model to monitor tip pressure of a medical instrument. According to one illustrative embodiment, a method 700 for determining force on a tip of the instrument includes a step 702 for receiving inputs from the instrument having at least one actuation member used to manipulate a position of the instrument while in a patient's body. The inputs may include the motor force, the motor position, and the instrument tip position. These inputs may be measured by various instruments as described above. For example, the instrument tip position may be determined by a fiber optic sensor.

The method further includes a step 704 for applying the inputs to a lumped model of the instrument. As described above, the lumped model includes a motor mass and a medical instrument mass associated with a portion of the instrument. These two masses interact with each other through spring and damping force forces. Additionally, these two masses involve frictional forces.

The method further includes a step 706 for determining a force on a tip of the instrument based on both the inputs and the lumped model. This may be performed in real time. Thus, based on the inputs and the lumped model, an operator can get a substantially accurate reading of the force being placed on the tip of the instrument, which in turn indicates the force on the patient's tissue. If the force exceeds a predefined value, then the operator can be notified accordingly.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 600. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method performed by a processing system, the method comprising:
    receiving at least one input from a medical instrument, the medical instrument including at least one elongated actuation member used to move at least a portion of the medical instrument; and
    determining a force on a tip of the medical instrument by applying the at least one input to a lumped model of the medical instrument, wherein the lumped model comprises:

a mass of a motor used to operate the at least one elongated actuation member; and a mass of at least a portion of a catheter body of the medical instrument.

2. The method of claim 1, wherein the force on the tip of the medical instrument is determined in real time.

3. The method of claim 2, further comprising, alerting an operator of the medical instrument if the force on the tip of the medical instrument exceeds a specified value.

4. The method of claim 1, wherein the at least one input comprises:

a motor torque applied by the motor;

a rotational position of a driveshaft of the motor; and a position of the tip of the medical instrument.

5. The method of claim 4, further comprising determining the position of the tip of the medical instrument with an optical fiber shape sensor.

6. The method of claim 1, wherein the lumped model further comprises:

a spring parameter coupling the mass of the motor to the mass of at least the portion of the catheter body; and a damping parameter coupling the mass of the motor to the mass of at least the portion of the catheter body.

7. The method of claim 1, wherein the lumped model further comprises:

a frictional parameter associated with the motor; and a frictional parameter associated with the catheter body.

8. The method of claim 1, wherein the lumped model further comprises:

a damping parameter coupling the mass of the motor to ground; and a damping parameter coupling the mass of at least the portion of the catheter body to ground.

9. The method of claim 1, wherein the lumped model further comprises an offset spring parameter coupling the mass of the at least a portion of the catheter body to ground.

10. A system comprising:

a medical instrument; and a computer system in communication with the medical instrument, the computer system being configured to:

receive at least one input from a motor coupled to an elongated actuation member of the medical instrument, the elongated actuation member being used to move a tip of the medical instrument;

receive at least one input indicating a position of the tip of the medical instrument;

determine a force applied to the tip of the medical instrument by applying the at least one input from the motor and the at least one input indicating the position of the tip to a lumped model of the medical instrument, wherein the lumped model comprises:

a mass of the motor; and a mass of at least a portion of the medical instrument.

11. The system of claim 10, wherein the force applied to the tip of the medical instrument is determined in real time.

12. The system of claim 10, wherein the computer system is further configured to cause the system to alert an operator of the medical instrument if the force applied to the tip of the medical instrument exceeds a specified value.

13. The system of claim 10, wherein the at least one input from the motor comprises:

a force applied to the motor; and a position of the motor.

14. The system of claim 10, wherein the input indicating the position of the tip of the medical instrument comprises information received from an optical fiber shape sensor.

15. The system of claim 10, wherein the lumped model further comprises:

a spring parameter coupling the mass of the motor to the mass of the portion of the medical instrument;

a damping parameter coupling the mass of the motor to the mass of the portion of the medical instrument including the tip of the medical instrument;

a frictional parameter associated with the motor;

a frictional parameter associated with the medical instrument;

a damping parameter coupling the mass of the motor to ground;

a damping parameter between the mass of the portion of the medical instrument including the tip of the medical instrument and ground; and an offset spring parameter between the mass of the tip of the medical instrument and ground.

16. A medical system comprising:

a medical instrument including a rotating member coupled to a catheter body through an elongated actuation member, a motor coupled to the medical instrument and configured to move the catheter body by applying a torque to the rotating member, which in turn applies a tension to the elongated actuation member;

a control system in communication with the medical instrument and with the motor, the control system being configured to:

receive an input indicating a rotational position of a driveshaft of the motor;

receive an input indicating a torque applied by the motor;

receive an input indicating a position of a tip of the catheter body; and determine, using a lumped model, a force applied to the tip of the catheter body, wherein the lumped model comprises:

a mass of the motor; and a mass of at least a portion of the catheter body.

17. The medical system of claim 16, wherein the control system is further configured to alert an operator of the medical system if the force applied to the tip of the catheter body exceeds a specified value.

18. The medical system of claim 16, wherein the lumped model comprises at least one of:

a spring parameter coupling the mass of the motor to the mass of at least the portion of the catheter body;

a damping parameter coupling the mass of the motor to the mass of at least the portion of the catheter body;

a frictional parameter associated with the motor;

a frictional parameter associated with the catheter body;

a damping parameter coupling the mass of the motor to ground;

a damping parameter coupling the mass of at least the portion of the catheter body to ground; or an offset spring parameter coupling the mass of the at least the portion of the catheter body to ground.

* * * * *